United States Patent [19]
Harris

[11] Patent Number: 4,583,967
[45] Date of Patent: Apr. 22, 1986

[54] TELESCOPING CATHETER SHUNT SYSTEM

[75] Inventor: Donald L. Harris, Key Largo, Fla.

[73] Assignee: Cordis Corporation, Miami, Fla.

[21] Appl. No.: 579,347

[22] Filed: Feb. 13, 1984

[51] Int. Cl.⁴ ............................................. A61M 27/00
[52] U.S. Cl. ........................................ 604/9; 604/247
[58] Field of Search ..................................... 604/8–10, 604/247

[56] References Cited

U.S. PATENT DOCUMENTS

| | | | |
|---|---|---|---|
| 3,623,484 | 11/1971 | Schulte | 128/350 |
| 3,889,687 | 6/1975 | Harris et al. | 604/247 |
| 3,991,768 | 11/1976 | Portnoy | 604/10 |
| 4,261,341 | 4/1981 | Hakim et al. | 604/9 |
| 4,382,445 | 5/1983 | Sommers | 604/8 |

Primary Examiner—P. E. Konopka
Attorney, Agent, or Firm—Henry W. Collins; Thomas R. Vigil

[57] ABSTRACT

The telescoping catheter shunt system comprises first and second telescoping tubings, the first tubing being connected to an anchoring connector mounted in a burr hole, the connector being connected to a catheter adapted to be inserted into a body cavity to be drained and being received within the second tubing which has a larger diameter than the first tubing. A valve assembly is connected to the second tubing and has a control mechanism for controlling the drainage of fluid from the cavity in response to pressure of the draining fluid. The first tubing has a flange at the proximal end thereof which has an outer diameter slightly greater than the inner diameter of the second tubing in which it is received to establish a friction fit between the outer surface of the flange and the inner surface of the second tubing that defines a primary seal for keeping body fluids other than the draining fluid out of the system. The second tubing has an annular stop member at the distal end thereof through which the first tubing extends such that upon telescoping of the tubings, relative movement between them is limited by engagement of the flange with the stop member so that the tubings cannot separate. The valve assembly is connected to a drainage catheter adapted to be positioned in a body cavity into which the draining fluid is deposited.

The method for draining fluid from a body cavity, e.g. ventricle of a child, utilizing the telescoping catheter shunt system defined above.

19 Claims, 4 Drawing Figures

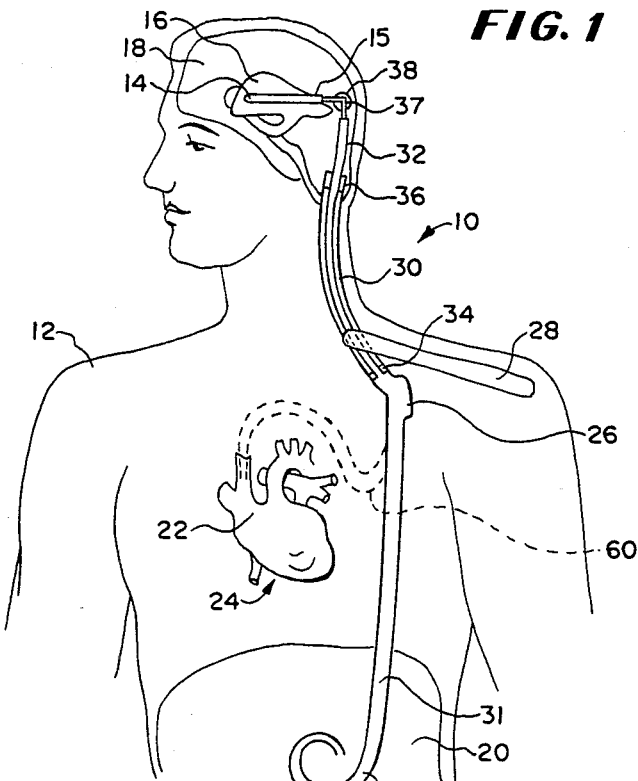
FIG. 1
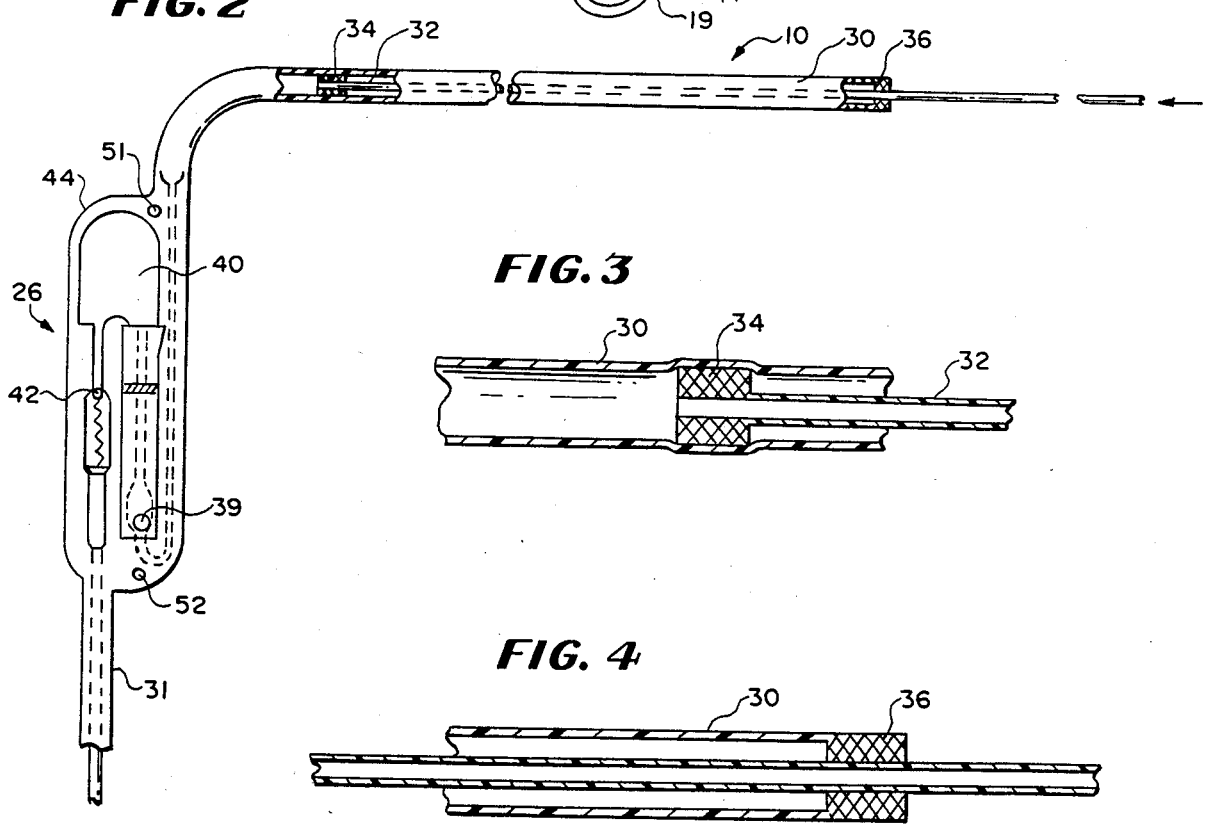
FIG. 2
FIG. 3
FIG. 4

TELESCOPING CATHETER SHUNT SYSTEM

FIELD OF THE INVENTION

The present invention relates to a catheter shunt system for draining fluid from a body cavity. More particularly, the present invention relates to a telescoping catheter shunt system which can accommodate the growth of a patient, such as the growth of a child.

DESCRIPTION OF THE PRIOR ART

Heretofore various telescoping catheter shunt systems for treatment of such conditions as hydrocephalus have been proposed to accommodate a period of growth of a patient and to facilitate replacement of the system after the period of growth.

Two such systems are disclosed in the following U.S. Patents:

| U.S. PAT. NO. | PATENTEE |
| --- | --- |
| 3,623,484 | Schulte |
| 4,382,445 | Sommers |

The Schulte U.S. Pat. No. 3,623,484 discloses one shunt system with growth capability, such capability being limited to no more than two inches. This short growth capability has not been proven to be practical.

The Sommers U.S. Pat. No. 4,382,445 discloses a telescoping shunt system with growth capabilities which will carry a patient from childhood into adolescence, or from various stages of adolescence to adulthood. The outer ends of the telescoping catheters are secured to the patient and the patient's growth applies a tensile force to the shunt system to cause relative movement between the telescoping inner ends. The inner end of the smaller diameter catheter has flexible flange gaskets which form a seal with the inner diameter of a larger diameter catheter when they are received in and flexed within the larger diameter catheter. A variable pressure valve is disclosed which is mountable at a burr hole in the skull.

As will be described in greater detail hereinafter, the telescoping catheter shunt system of the present invention provides a catheter shunt system with growth potential. Further, with the construction of the telescoping catheter shunt system defined herein, undesirable displacement of the shunt system (common in infants) is prevented. Still further, the catheter shunt system of the present invention includes a valve mechanism which is mountable at a position within the body of the patient rather than on the skull as provided in previous shunt systems thereby eliminating the problems encountered during cat scanning of the head of the patient. Further, with the shunt system of the present invention, radio-opaque markers are used to determine the location of the ends of the telescoping tubes forming the telescoping catheter shunt system of the present invention. As a result, metallic parts of the system are not placed in the cranium and are only positioned within the chest cavity and/or abdominal cavity.

SUMMARY OF THE INVENTION

According to the invention there is provided a telescoping catheter shunt system comprising first and second telescoping tubings, said first tubing being coupled to a catheter adapted to be inserted into a body cavity to be drained and being received within said second tubing which has a larger diameter than said first tubing, a valve assembly which is mounted to said second tubing and which has means for controlling the drainage of fluid from the cavity in response to pressure of the draining fluid and flexible means that can be pressed from an area external to the body to provide a flushing/pumping action, said first tubing having a seal forming and stop forming flange at the proximal end thereof which has an outer diameter slightly greater than the inner diameter of said second tubing in which it is received to establish a friction, sealing fit between the outer surface of said flange and the inner surface of said second tubing that defines a primary seal for keeping body fluids other than the draining fluid out of said system, said second tubing having an annular stop member at the distal end thereof through which said first tubing extends such that upon telescoping of the tubings, relative movement between them is limited by engagement of said flange with said annular stop member to prevent disengagement of the tubings so that said tubings cannot separate, the proximal end of said second tubing being attached to the said valve assembly, and a lower drainage catheter being attached to said valve assembly and positioned in a body cavity into which the draining fluid is to be deposited.

Further according to the invention there is provided a method for draining fluid from a body cavity utilizing a telescoping catheter shunt system of the type including first and second telescoping tubings, said first tubing being coupled to a catheter adapted to be inserted into a body cavity to be drained and being received within said second tubing which has a larger diameter than said first tubing, a valve assembly which is mounted to said second tubing and which has means for controlling the drainage of fluid from the cavity in response to pressure of the draining fluid and flexible means that can be pressed from an area external to the body to provide a flushing/pumping action, said first tubing having a seal forming and stop forming flange at the proximal end thereof which has an outer diameter slightly greater than the inner diameter of said second tubing in which it is received to establish a friction, sealing fit between the outer surface of said flange and the inner surface of said second tubing that defines a primary seal for keeping body fluids other than the draining fluid out of said system, said second tubing having an annular stop member at the distal end thereof through which said first tubing extends such that upon telescoping of the tubings, relative movement between them is limited by engagement of said flange with said annular stop member to prevent disengagement of the tubings so that said tubings cannot separate, the proximal end of said second tubing being attached to the said valve assembly, and a lower drainage catheter being attached to said valve assembly and positioned in a body cavity into which the draining fluid is to be deposited, said method comprising the steps of: positioning the valve assembly through a small incision of the skin in a selected location on the chest; tunneling and installing the drainage catheter under the skin to a second incision over the peritoneal entry site where any excess drain catheter is placed into the peritoneum; making a third incision over the burr hole location on the head; performing a second tunneling operation to pull the pre-assembled telescoping tubings from the valve assembly to the burr hole location, care being taken to assure the telescoping tubings are completely telescoped; making a burr hole in the skull; installing a ventricular catheter into the ventricles of the brain; trimming the ventricular catheter and the telescoping first tubing to a desired length; and securely fastening the ventricular catheter and the first tubing to a right angle connector mounted through the burr hole thereby anchoring one end of the telescoping catheter system to the burr hole and the other end to the valve in the chest at the location of the valve assembly.

BRIEF DESCRIPTION OF THE DRAWINGS

FIG. 1 is an AP sectional view of the human body showing the telescoping catheter shunt system of the present invention implanted therein with the distal end of the system positioned within a ventricle of the brain and the proximal end positioned within the peritoneum or, in the alternative, within an atrium of the heart as shown in phantom.

FIG. 2 is a plan view of the catheter shunt system and valve assembly thereof prior to insertion of the system in a patient and with a portion broken away to show an end of a smaller telescoping tubing inside a larger tubing.

FIG. 3 is a sectional view of the proximal end of the smaller tubing within the larger tubing.

FIG. 4 is a sectional view of the distal end of the larger tubing with the smaller tubing passing therethrough.

DESCRIPTION OF THE PREFERRED EMBODIMENT

Referring now to FIG. 1 in greater detail there is illustrated a telescoping catheter shunt system 10 made in accordance with the teachings of the present invention implanted within a body 12 of an adult. As shown, a distal end 14 of a ventricular catheter/tubing 15 of the shunt system 10 is positioned within a cranial cavity 16, such as a ventricle 16 of a brain 18, in the body 12 from which fluid is to be drained. More specifically, fluid is drained from the ventricle 16 of the brain 18, to provide a drainage for excessive cerebrospinal fluid produced in a patient having a condition referred to as hydrocephalus.

The fluid being drained from the ventricle 16 in the brain 18 is shunted by a proximal drainage catheter/tubing 19 of the shunt system 10 to a peritoneum 20 in the body 12 or in the alternative, to an atrium 22 of a heart 24 as shown in phantom in FIG. 1.

Further as shown in FIG. 1, the shunt system 10 is provided with a valve assembly 26 which is anchored at a desired location within the chest and which will be described in greater detail in connection with the description of FIG. 2 below. As shown the valve assembly 26 is positioned just below the clavicle 28 within the body 12.

The telescoping catheter shunt system 10 of the present invention comprises a lower larger in diameter catheter/tubing 30 in which is received an upper smaller in diameter telescoping catheter/tubing 32. With this construction, the system 10 is capable of accommodating a human growth capacity of any desired height (length). This is accomplished by providing an excess of the drainage catheter 19 within the peritoneal cavity 20, such drainage catheter 19 permitting lengthening of a trunk portion 31 of the catheter 19 below the level where the valve assembly 26 is anchored, and by making the drainage catheter 19, and the telescoping catheters 30 and 32 of a desired length.

As shown in FIG. 2, the lower end of the tubing 32 has an end flange 34 thereon, the end flange 34 having a diameter slightly greater than the inner diameter of the tubing 30 within which it is received. By providing the flange 34 with a slightly greater diameter a primary seal for the system 10 is formed between flange 34 and the tubing 30 by reason of the frictional engagement between the end flange 34 and the tubing 30.

As shown in FIG. 4, the upper end of the tubing 30 is provided with an inwardly extending flange or annular stop member 36 which fits snugly about the tubing 32 traveling within the tubing 30. This snug fit provides a secondary seal for the system 10.

As the two tubings 30 and 32 are telescoped to their limits and the two flanges 34 and 36 come together, the maximum length of the telescoping catheter system 10 is achieved. In one preferred embodiment such growth potential or distance between the flanges 34, 36 is 8 to 10 inches and provides for replacement of the system 10 within a patient only once every 10 years or so until the patient reaches his maximum adult height.

By the provision of the two flanges 34 and 36, the system 10 is kept intact during the patient's growth and the two tubings 30 and 32 cannot telescope out of one another, thus preventing displacement of the system 10.

The ventricular catheter 15 extends from the ventricle 16 in the brain 18 and is anchored to a right angle connector 37 which extends through a burr hole 38 formed in the cranium. The upper tubing 32 is also anchored to the right angle connector 37. Then the upper tubing 32 is telescopically received within the lower tubing 30 of larger diameter which travels to the valve assembly 26. The drainage catheter 19 which is anchored to the valve assembly 26 extends down the body 12 from a position just below the clavicle 28 in a desired course to one of several locations where fluid being drained is deposited.

The valve assembly 26 controls the pressure of fluid remaining within the ventricles 16 of the brain 18 so that the ventricles 16 do not collapse from the removal of an excessive amount of fluid therefrom. In other words, the valve assembly 26 is pressure sensitive and operates only when an excessive fluid pressure is sensed by the valve assembly 26 as explained below.

As shown in FIG. 2, the valve assembly 26 utilized with the telescoping catheter assembly 10 of the present invention is a modified Horizontal-Vertical (HV) valve 26. Such HV valve 26 provides for pressure sensitivity and flushing of fluid not only when a patient is in a vertical or standing position but also when the patient is in the prone or lying down position. A similar valve assembly is disclosed in U.S. Pat. No. 3,889,687 issued to Don Harris for: SHUNT SYSTEM FOR TRANSPORT OF CEREBROSPINAL FLUID.

The valve assembly 26 includes a first ball valve 39 which is forced upwardly under pressure from the liquid draining from the ventricle 16 to allow the liquid to flow into a flushing chamber 40. Here liquid collects until the pressure of the liquid forces a second, spring-biased ball valve 42 downwardly to allow fluid to flow to the location where it is deposited. The spring biased-valve 42 prevents back-flow when the patient is lying down.

The valve assembly 26 utilized with the shunt system 10 of the present invention differs slightly from the valve assembly disclosed in U.S. Pat. No. 3,889,687 by having the flushing chamber 40. An outer wall 44 of the flushing chamber 40 is flexible and preferably is positioned just below the clavicle 28 and can be pressed from an area external to the body to provide a flushing-/pumping action with the valve assembly 26.

As in conventional shunting valve mechanisms, the valve assembly 26 of the present invention is constructed to allow not only fluid to pass therethrough but also allows for the passage of proteinaceous debris and blood cells forming sediment commonly found in cerebrospinal fluid.

Preferably the flange 34 at the proximal end of the small diameter tubing 32 is made of a radio-opaque material. This flange 34 serves not only to provide a primary seal for the telescoping catheter shunt system 10 by being of a diameter slightly greater than the inner diameter of the larger diameter tubing 30 within which it is received but also a a marker to indicate the telescoping travel of the tubing 30 during the patient's growth. The growth then can be monitored by non-invasive X-ray techniques.

It will be readily understood that stop member 36 prevents the two tubings 30 and 32 forming the telescoping catheter shunt system 10 from becoming disengaged and therefore alleviates the problem of displacement of the catheter system 10 during growth of the patient. Further by providing a snug fit between the stop member 36 and the upper smaller diameter tubing 32, the secondary seal is provided for keeping invasive body fluids out of the system 10.

With the provision of the two seal forming members 34, 36, a fluid tight assembly is provided and, because of the friction fit of the flange 34 at the lower end of the small diameter tubing 32 within the larger tubing 30, pulling forces resulting from the patient's growth are required to pull the tubing 32 slowly out of the tubing 30 thus preventing the slipping of the two tubings 30 and 32 in and out of each other.

In other words, as the patient grows, there is a pulling force exerted at the positions where the telescoping catheter shunt system 10 is secured to the body 12. This pulling force acts against the friction fit of the flange 34 in the tubing 30 so that the tubings 30 and 32 telescope incrementally and there is no possibility of an excess of telescoping which could create a condition where one of the tubings could be crimped.

When the two tubings 30 and 32 are telescoped to the furthest extent possible, the stop member 36 acts against the flange 34 provided in the inner tubing 32 to keep the two tubings 30 and 32 from separating. Such separation is not desirable because if the tubings separate, the fluid that is being drained from the cavity could be shunted to an undesirable location, i.e., wherever the end of the first tube is, and may cause complications, such complications being caused by excess drainage fluid being allowed to collect in an area or cavity of the body from which it cannot escape or from which it cannot be assimilated back into the body.

The catheter shunt system 10 also accommodates growth at the area into which the fluid is being drained by the provision of an excess of the lower tubing 19 in the cavity 20. As the patient grows, the excess tubing, which is usually coiled within the cavity 20, can unwind and accommodate the patient's growth below the area at which the valve assembly 26 is attached.

The valve assembly 26 is attached at a level in the body 12 just below the clavicle 28, such attachment being made by suturing the valve assembly 26 to body tissue. To allow the suturing of the valve mechanism 26 to the body 12, two suture holes 51 and 52 are provided in the valve assembly 26.

In the alternative embodiment shown in FIG. 1, where the drainage of fluid is directly into the atrium of a heart, an excess 60 of tubing 19 is also provided so that the shunt system 10 does not become displaced. If it were to become displaced, the tubing will become clogged with blood clot and not drain properly, requiring replacement.

From the foregoing description, it will be apparent that the catheter shunt system 10 of the present invention has a number of advantages, some of which have been described above and others of which are inherent in the invention. Also, modifications can be made to the invention without departing from the teachings of the invention. Accordingly, the scope of the invention is only to be limited as necessitated by the accompanying claims.

I claim:

1. A telescoping catheter shunt system comprising first and second telescoping tubings, said first tubing being coupled to a catheter adapted to be inserted into a body cavity to be drained and being received within said second tubing which has a larger diameter than said first tubing, a valve assembly which is mounted to said second tubing and which has means for controlling the drainage of fluid from the cavity in response to pressure of the draining fluid and flexible means that can be pressed from an area external to the body to provide a flushing/pumping action, said first tubing having a seal forming and stop forming flange at the proximal end thereof which has an outer diameter slightly greater than the inner diameter of said second tubing in which it is received to establish a friction, sealing fit between the outer surface of said flange and the inner surface of said second tubing that defines a primary seal for keeping body fluids other than the draining fluid out of said system, said second tubing having an annular stop member at the distal end thereof through which said first tubing extends such that upon telescoping of the tubings, relative movement between them is limited by engagement of said flange with said annular stop member to prevent disengagement of the tubing so that said tubings cannot separate, the proximal end of said second tubing being attached to the said valve assembly, and a lower drainage catheter being attached to said valve assembly and positioned in a body cavity into which the draining fluid is to be deposited.

2. The system of claim 1 wherein said annular stop member is made of a radio-opaque material.

3. The system of claim 1 wherein said flange is made of a radio-opaque material.

4. The system of claim 1 wherein said valve assembly includes a body having a flushing/pumping chamber therein.

5. The system of claim 4 wherein said body has a flexible thin wall adjacent said chamber which wall forms said flexible means that can be depressed from outside the body to flush/pump fluid from said chamber.

6. The system of claim 1 wherein said tubings have overall lengths such that on insertion of the system in a body, the distance between said flange and said stop member is from 7 to 11 inches.

7. The system of claim 1 wherein said annular stop member fits snugly around said first tubing to form a secondary seal to keep body fluids other than the draining fluid out of said system.

8. The system of claim 4 wherein said valve assembly has a first gravity actuated ball valve therein.

9. The system of claim 4 wherein said valve assembly has a second spring biased ball valve therein.

10. The system of claim 4 wherein said valve assembly has two suture holes in said body.

11. The system of claim 1 including a catheter, and a right angle connector adapted to be mounted in said burr hole with one end of said connector being connected to said catheter which can be positioned in the cavity to be drained and the other end of said connector being connected to said first tubing.

12. A method for draining fluid from a body cavity utilizing a telescoping catheter shunt system of the type including first and second telescoping tubings, said first tubing being coupled to a catheter adapted to be inserted into a body cavity to be drained and being received within said second tubing which has a larger diameter than said first tubing, a valve assembly which is mounted to said second tubing and which has means for controlling the drainage of fluid from the cavity in response to pressure of the draining fluid and flexible means that can be pressed from an area external to the body to provide a flushing/pumping action, said first tubing having a seal forming and stop forming flange at the proximal end thereof which has an outer diameter slightly greater than the inner diameter of said second tubing in which it is received to establish a friction, sealing fit between the outer surface of said flange and the inner surface of said second tubing that defines a primary seal for keeping body fluids other than the draining fluid out of said system, said second tubing having an annular stop member at the distal end thereof through which said first tubing extends such that upon telescoping of the tubings, relative movement between them is limited by engagement of said flange with said annular stop member to prevent disengagement of the tubings so that said tubings cannot separate, the proximal end of said second tubing being attached to the said valve assembly, and a lower drainage catheter being atached to said valve assembly and positioned in a body cavity into which the draining fluid is to be deposited, said method comprising the steps of: positioning the valve assembly through a small incision of the skin in a selected location on the chest; tunneling and installing the drainage catheter under the skin to a second incision over the peritoneal entry site where any excess drain catheter is placed into the peritoneum; making a third incision over the burr hole location on the head; performing a second tunneling operation to pull the pre-assembled telescoping tubings from the valve assembly to the burr hole location, care being taken to assure the telescoping tubings are completely telescoped; making a burr hole in the skull; installing a ventricular catheter into the ventricles of the brain; trimming the ventricular catheter and the telescoping first tubing to a desired length; and securely fastening the ventricular catheter and the first tubing to a right angle connector mounted through the burr hole thereby anchoring one end of the telescoping catheter system to the burr hole and the other end to the valve in the chest at the location of the valve assembly.

13. The method of claim 12 wherein said valve assembly is mounted at a position in the body just below the clavicle.

14. The method of claim 12 wherein said body cavity is the peritoneal cavity.

15. The method of claim 13 wherein said body cavity is the atrium.

16. The method of claim 15 wherein an excess of drainage catheter is provided in the body cavity.

17. The method of claim 16 wherein said excess of drainage catheter is coiled at its proximal end in the body cavity.

18. The method of claim 12 wherein said first and second tubings have sufficient lengths such that the tubings can telescope from 7 to 11 inches during the growth of the patient.

19. The method of claim 12 wherein said flange and said stop member are made from a radio-opaque material so that their positions can be determined within the body by X-ray techniques or cat scan techniques.

* * * * *